United States Patent
Lissoni

(10) Patent No.: US 10,957,440 B2
(45) Date of Patent: Mar. 23, 2021

(54) REUSABLE DISPOSABLE AND DIALYSIS APPARATUS THEREFOR

(71) Applicant: FRESENIUS MEDICAL CARE DEUTSCHLAND GMBH, Bad Homburg (DE)

(72) Inventor: Fabio Lissoni, Frankfurt am Main (DE)

(73) Assignee: Fresenius Medical Care Deutschland GmbH, Bad Homburg (DE)

(*) Notice: Subject to any disclaimer, the term of this patent is extended or adjusted under 35 U.S.C. 154(b) by 0 days.

(21) Appl. No.: 15/771,146

(22) PCT Filed: Oct. 27, 2016

(86) PCT No.: PCT/EP2016/075983
§ 371 (c)(1),
(2) Date: Apr. 26, 2018

(87) PCT Pub. No.: WO2017/072258
PCT Pub. Date: May 4, 2017

(65) Prior Publication Data
US 2018/0314851 A1   Nov. 1, 2018

(30) Foreign Application Priority Data
Oct. 27, 2015   (EP) .................................... 15191573

(51) Int. Cl.
*G16H 20/40*   (2018.01)
*G16H 40/20*   (2018.01)
*G16H 10/65*   (2018.01)
*G06F 21/62*   (2013.01)

(52) U.S. Cl.
CPC ......... *G16H 20/40* (2018.01); *G06F 21/6245* (2013.01); *G16H 10/65* (2018.01); *G16H 40/20* (2018.01)

(58) Field of Classification Search
CPC . G06F 21/6245; G06F 19/3481; G16H 10/65; G16H 40/20
(Continued)

(56) References Cited

U.S. PATENT DOCUMENTS 6,050,278 A * 4/2000 Arnal .................... A61M 1/168
                                                    134/167 R
6,895,490 B1 * 5/2005 Moore .................. G06F 3/0607
                                                    365/230.03
(Continued)

FOREIGN PATENT DOCUMENTS

WO    0228531 A1    4/2002
WO    2004023389 A2 3/2004

OTHER PUBLICATIONS

International Search Report and Written Opinion issued in corresponding International Patent Application No. PCT/EP2016/075983 dated Jan. 25, 2017 (15 pages).

*Primary Examiner* — Badrinarayanan Champakesan
(74) *Attorney, Agent, or Firm* — Kilyk & Bowersox, P.L.L.C.

(57) ABSTRACT

The invention pertains to a reusable disposable (1) for usage within a medical treatment process by a corresponding medical apparatus (A) and a corresponding medical apparatus. The reusable disposable (1) for usage within a medical process by a medical apparatus (A), the reusable disposable (1) comprises first memory means ($MEM_1$) for storing predetermined data, whereby the first memory means are programmed during production of the reusable disposable (1), whereby the first memory means ($MEM_1$) are secured against any or any unauthorized alteration after production, second memory means ($MEM_2$) for storing patient identity data, whereby the second memory means is a write-once
(Continued)

memory, whereby re-usage of the reusable disposable is only allowed with respect to same patient identity data.

15 Claims, 1 Drawing Sheet

(58) Field of Classification Search
USPC .......................................................... 726/26
See application file for complete search history.

(56) References Cited

U.S. PATENT DOCUMENTS

| | | | | |
|---|---|---|---|---|
| 7,573,370 B2* | 8/2009 | Becker | ............... | G06K 19/0717 340/10.1 |
| 8,255,655 B2* | 8/2012 | Yu | ...................... | G06F 12/1433 711/163 |
| 8,266,366 B2* | 9/2012 | Fruin | ................... | G06F 3/0634 711/103 |
| 2005/0189219 A1* | 9/2005 | Amirkhanian | ... | G01N 27/44704 204/403.01 |
| 2005/0240613 A1* | 10/2005 | Logan, Jr. | ............... | G16H 10/65 |
| 2005/0251695 A1* | 11/2005 | Jaquette | ............... | G11B 27/328 713/194 |
| 2007/0122314 A1* | 5/2007 | Strand | ................. | B29C 65/1696 422/400 |
| 2009/0151479 A1* | 6/2009 | Bartel | ................... | G16H 40/20 73/864.51 |
| 2009/0199301 A1* | 8/2009 | Chandrasekaran | ......................... | G06F 16/2358 726/27 |
| 2015/0238673 A1* | 8/2015 | Gerber | ............... | A61M 1/1696 210/85 |
| 2015/0359954 A1* | 12/2015 | Gerber | .................... | A61M 1/36 210/647 |

* cited by examiner

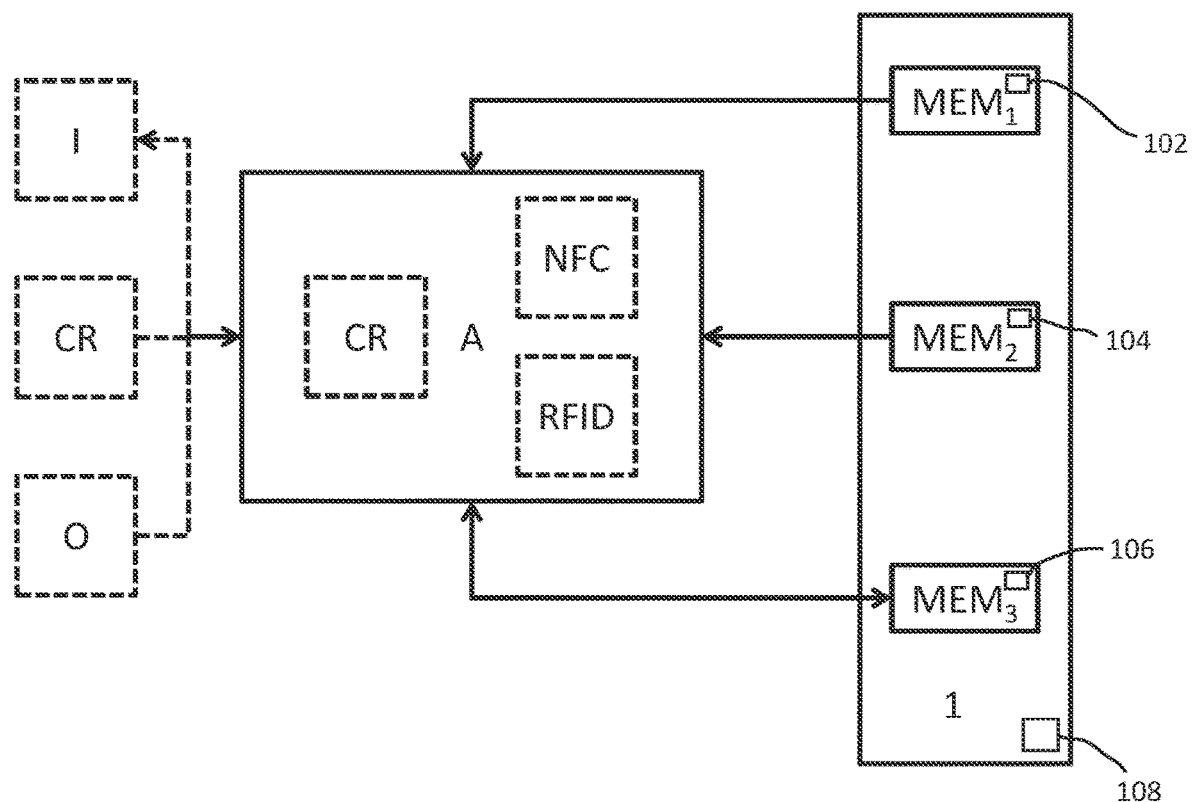

REUSABLE DISPOSABLE AND DIALYSIS APPARATUS THEREFOR

This application is a National Stage Application of PCT/EP2016/075983, filed Oct. 27, 2016, which claims priority to European Patent Application No. 15191573.3, filed Oct. 27, 2015.

BACKGROUND

In recent years the Numbers of patients requiring external processing of blood is sharply increasing. Processing of blood may be due because of e.g. failure or insufficient performance of kidney(s) and/or liver or for other reasons.

Due to this increasing number of patients as well as due to a need for less expensive care, specialized centers performing renal dialysis and/or liver dialysis as well as home care equipment were developed in the past.

Many of the resources employed during treatment may be reused. Some of those devices may need to be sterilized at one or more occasions. Other parts may be used only once.

Nevertheless there exist parts which could be reused in principle but which could not sterilized easily. In addition, while sterilization would be available for some of those parts in principle, the costs associated therewith might exceed the cost for a replacement part.

WO 02/28531 A1 shows a fluid separation conduit cartridge with encryption capabilities which is enabled to decrypt encrypted information received from an analytical system or an operating facility in communication with the conduit cartridge. The system nor its parts are patient related but relate to the interaction of the system and the cartridge.

Due to patient safety requirements reuse of parts which could not be sterilized is not recommended leading to a situation where valuable parts are disposed while they could have been reused.

Therefore, there is a need for a solution providing patient security while allowing reuse of those parts which would otherwise be disposed after single usage.

BRIEF DESCRIPTION OF THE INVENTION

The invention therefore proposes a reusable disposable for usage within a dialysis process by a dialysis apparatus. The reusable disposable comprises first memory means for storing predetermined data, whereby the first memory means are programmed during production of the reusable disposable, whereby the first memory means are secured against any or any unauthorized alteration after production. The reusable disposable further comprises second memory means for storing patient identity data, whereby the second memory means is a write-once memory, whereby re-usage of the reusable disposable is only allowed with respect to same patient identity data.

By means of the invention, it is ensured that patient safety is maintained while allowing for a re-usage, which could also be understood as a prolonged usage, of parts which would otherwise be disposed after single usage.

In an embodiment of the invention, the first memory means comprise a hardware lock preventing alteration of data contained in the first memory means after storage.

Hardware locks are particularly beneficial as a reverse engineering requires highly sophisticated machinery thereby representing a valuable security hurdle.

According to another embodiment of the invention the first memory means comprise a software lock preventing unauthorized alteration of data contained in the first memory means after storage.

Software locks may be easily programmed and allow for a quick adaption in case of a detected security problem.

According to still another embodiment of the invention the first memory means comprise data selected from a group comprising brand, article number, lot, security code.

By allowing for storing these data, a variety of production and product related data may be securely stored and may not be altered after selling thereby improving security and thereby impeding piracy and forgery.

According to still another embodiment the first memory means comprise data selected from a group comprising maximum number of usages, maximum run time, best before date, security code.

By allowing for storing these data, a variety of production and product related data may be securely stored and may not be altered after selling thereby improving security and thereby impeding piracy and forgery.

According to yet another embodiment the reusable disposable further comprise third memory means, whereby the third memory means comprise data selected from a group comprising a log of treatment related data.

By allowing for storing treatment related data it may be provided for a self-secure system allowing usage within certain constraints irrespective of the dialysis apparatus to be used there with.

According to a further embodiment the third memory means comprise a software lock preventing unauthorized alteration of data contained in the second memory means after storage.

According to still another embodiment, the second memory means comprise a software lock preventing unauthorized alteration of data contained in the second memory means after storage.

Software locks may be easily programmed and allow for a quick adaption in case of a detected security problem.

In a further embodiment of the invention re-usage is controlled by the reusable disposable.

By allowing for controlling re-usage by the reusable disposable it may be provided for a self-secure system allowing usage irrespective of the dialysis apparatus to be used there with.

The invention also proposes a dialysis apparatus for usage of reusable disposable as detailed before within a dialysis process. The dialysis apparatus comprises means for reading data from first memory means of said reusable disposable, means for reading from second memory means of said reusable disposable, whereby re-usage of the reusable disposable is only allowed with respect to same patient identity data.

According to an embodiment the dialysis apparatus comprises means for storing data in the third memory means.

By allowing for storing treatment related data it may be provided for a self-secure system allowing usage within certain constraints irrespective of the dialysis apparatus to be used there with.

According to another embodiment the third memory means comprise a software lock preventing unauthorized alteration of data contained in the third memory means after storage.

Software locks may be easily programmed and allow for a quick adaption in case of a detected security problem.

In a further embodiment of the invention re-usage is controlled by the dialysis apparatus.

By allowing for controlling re-usage by the dialysis apparatus it may be provided for a secured system allowing usage respective of the dialysis apparatus to be used there with.

In yet a further embodiment of the invention the dialysis apparatus further comprises a display for displaying data stored in the first memory means and/or second memory means and/or third memory means.

Providing such data may allow for an easy control of data and may also allow for displaying remaining usage data and/or patient or treatment (log) data.

According to yet another embodiment the dialysis apparatus further comprises means for inputting data for storing in said second memory means and/or third memory means, whereby the third memory means comprise data selected from a group comprising a log of treatment related data.

Provisioning of input means allow for entering security codes, patient identity data, and treatment data and may therefore enhance security of the devices.

In yet a further embodiment said means for inputting comprise a card reader and/or a NFC reader and/or an RFID reader.

By usage of these inputting means, also data from the disposable may be read as well as data related to a patient may be read allowing for an In yet another embodiment re-usage is controlled by the dialysis apparatus.

By allowing for controlling re-usage by the dialysis apparatus it may be provided for a secured system allowing usage respective of the dialysis apparatus to be used there with.

BRIEF DESCRIPTION OF THE FIGURE

FIG. 1 shows a schematic overview according to several aspects of the invention.

DETAILED DESCRIPTION

The present disclosure describes preferred embodiments with reference to the Figures, in which like reference signs represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the description, numerous specific details are recited to provide a thorough understanding of embodiments of the invention.

I.e., unless indicated as alternative only any feature of an embodiment may also be utilized in another embodiment.

In addition, even though at some occurrences certain features will be described with reference to a single entity, such a description is for illustrative purpose only and actual implantations of the invention may also comprise one or more of these entities. I.e. usage of singular also encompasses plural entities unless indicated.

In the following the invention will be described with reference to a dialysis treatment and a corresponding dialysis apparatus and respective disposable(s) used therein. However, the invention is not limited to dialysis and may also be used in any kind of medical treatment processes provisioned by respective medical apparatuses and corresponding disposables used within the treatment processes by said apparatuses.

In FIG. 1 a schematic overview according to several aspects of the invention is shown.

A reusable disposable 1 for usage within a dialysis process by a dialysis apparatus A is schematically shown. The reusable disposable 1 may be any kind of disposable needed for treatment of a patient, e.g. a cassette comprising pumps and/or membrane as well as portions thereof. Accordingly, reusable disposable 1 can comprise a valve, a pump, a membrane, or a combination (108) thereof.

The reusable disposable 1 comprise first memory means $MEM_1$ for storing predetermined data, whereby the first memory means are programmed during production of the reusable disposable 1, whereby the first memory means $MEM_1$ are secured against any or any unauthorized alteration after production.

Techniques which could be used are e.g. memories of the write-once type, which are e.g. used in (microcontroller) chipcards, or securing technologies also known as digital rights management, which may be used on SD-Card like memories.

The reusable disposable 1 further comprise second memory means for storing patient identity data, whereby the second memory means are adapted to be changed only once, e.g. the second memory means is a write-once memory, whereby re-usage of the reusable disposable is only allowed with respect to same patient identity data.

Write-once memory is known since long. For example it is known to use fuse like structures which may be "programmed" by blowing a fuse. These techniques have been successfully used within chipcards. Also certain type of Secure Digital Flash Memory is known.

It is up to the system design whether a re-usage is allowed by the disposable 1 and/or the machine A, within which the disposable 1 is used.

By means of the invention, it is ensured that patient safety is maintained while allowing for a re-usage, which could also be understood as a prolonged usage, of parts which would otherwise be disposed after single usage.

That is, a patient may use his cassette for one or more treatments, while another patient may not use the same cassette. By inhibiting use of a cassette by another patient, safety for both patients is enhanced as no patient may use a cassette not being designated to him. I.e. after first usage of a disposable, the disposable is personalized. That is, why the second memory means containing patient related data may only be written once.

The first memory means $MEM_1$ may comprise a hardware lock preventing alteration of data contained in the first memory means after storage.

Hardware locks are particularly beneficial as a reverse engineering requires highly sophisticated machinery thereby representing a valuable security hurdle. I.e. by making reverse engineering expensive and time-consuming the risk of fraudulent/unauthorized acts is diminished.

The first memory means $MEM_1$ may alternatively or additionally comprise a software lock (102) preventing unauthorized alteration of data contained in the first memory means after storage.

Software locks may be easily programmed and allow for a quick adaption in case of a detected security problem.

In an advantageous embodiment the first memory means $MEM_1$ may comprise data selected from a group comprising brand, article number, lot, security code.

By allowing for storing these data, a variety of production and product related data may be securely stored and may not be altered after selling thereby improving security and thereby impeding piracy and forgery.

The first memory means $MEM_1$ may alternatively or additionally also comprise data selected from a group comprising maximum number of usages, maximum run time, best before date, security code.

By allowing for storing these data, a variety of production and product related data may be securely stored and may not be altered after selling thereby improving security and thereby impeding piracy and forgery.

Some of these data may be subject to national regulations. E.g. the best-before-date may be subject to national regulations leading to a situation where same products produced on the same day may have differing best-before date because of different destination markets. As these data may be stored once before being shipped, the respective data can be provided as necessary.

Furthermore, some embodiments of a reusable disposable 1 may also offer third memory means, whereby the third memory means $MEM_3$ comprise data selected from a group comprising a log of treatment related data.

The logging may be performed internally by the reusable disposable 1 and/or it may be performed by the dialysis machine A used in connection with the reusable disposable 1. Logging as such may be performed continuously and/or at the end of a treatment period.

By allowing for storing treatment related data it may be provided for a self-secure system allowing usage within certain constraints irrespective of the dialysis apparatus to be used there with.

Again, the third memory means $MEM_3$ may comprise a software lock preventing unauthorized alteration of data contained in the third memory means after storage.

Also, the second memory means $MEM_2$ may comprise a software lock (104) preventing unauthorized alteration of data contained in the second memory means after storage.

Software locks may be easily programmed and allow for a quick adaption in case of a detected security problem.

Software locks may be embodied by respective commands, and/or passwords.

According to an aspect of the invention both the reusable disposable 1 as well as the dialysis machine A may control re-usage of the reusable disposable 1.

E.g. the reusable disposable 1 may subject to identifying the same patient allow usage e.g. by allowing actuation of certain elements by the dialysis apparatus. For example, the re-usable disposable 1 may inhibit a flow of fluid by not opening a valve or not engaging a pump to be actuated via the dialysis machine A.

Alternatively or additionally also the dialysis machine A may subject to identifying the same patient allow usage e.g. by allowing actuation of certain elements by the dialysis apparatus. For example, if there is a match of data, the dialysis machine will actuate a valve and/or pump provided within the reusable disposable 1.

Likewise, other data may also allow for operation or lead to a stop of operation. Such data may be a lapse of best-before-date, a maximum usage period after first usage, a maximum number of operations, a maximum number of usages, reaching a minimum of consumables, reaching a maximum of spent consumables, reaching a maximum of stored disposables.

By allowing for controlling re-usage it may be provided for a secured system allowing usage respective of the dialysis apparatus to be used there with.

Likewise, a dialysis apparatus A for usage of reusable disposable 1 comprises means for reading data from first memory means $MEM_1$ of said reusable disposable 1, means for reading from second memory means $MEM_2$ of said reusable disposable 1, whereby re-usage of the reusable disposable is only allowed with respect to same patient identity data.

Said means for reading data correspond to the type of memory and the interface for accessing the memory/memories.

I.e., suppose that the interface is an RFID interface, then the dialysis machine A may comprise an RFID reader for accessing the data. Such an interface may be located in close vicinity to a corresponding interface provided by the reusable disposable 1 thereby allowing to read only data of reusable disposables engaged with the dialysis machine A.

If the data is e.g. stored in a chip like structure such as the ones known from (microcontroller) chipcards, than the interface may be embodied in a chipcard reader like interface allowing for accessing memories provided within the reusable disposable 1.

I.e. the actual interface may have different nature and may be a direct electrical link, a wireless link and/or an optical link.

As described previously in some embodiments the reusable disposable may support writing of data during or after treatment of a patient. Consequently also a dialysis apparatus A may comprises means for storing data in the third memory means $MEM_3$.

By allowing for storing treatment related data it may be provided for a self-secure system allowing usage within certain constraints irrespective of the dialysis apparatus A to be used there with.

Again, as the third memory means $MEM_3$ may comprise a software lock (106) preventing unauthorized alteration of data contained in the third memory means after storage, the dialysis machine A may comprise corresponding means to actuate said software lock in order to enter data in a secure manner. E.g. there may be a handshaking provisioned.

Software locks may be easily programmed and allow for a quick adaption in case of a detected security problem. Note, security mechanism may be updated within the dialysis machine A e.g. via firmware updates.

Obviously, a dialysis apparatus A may further comprise a display O for displaying data stored in the first memory means $MEM_1$ and/or second memory means $MEM_2$ and/or third memory means $MEM_3$.

Providing such data may allow for an easy control of data and may also allow for displaying remaining usage data and/or patient or treatment (log) data.

Furthermore, the display may be used in order to provide instructions to a patient to enter data such as patient identity data or data enabling writing of data to a third memory $MEM_3$. The display may be any kind of a LCD, LED or E-Paper display.

Consequently a dialysis apparatus A may further comprise means for inputting I data for storing in said second memory means $MEM_2$ and/or third memory means, whereby the third memory means $MEM_3$ comprise data selected from a group comprising a log of treatment related data.

Again the input device may also be used for entering patient related data and/or data enabling writing of data to a third memory $MEM_3$. The means for inputting may be provided by any kind of a keyboard and/or reader as will be detailed later.

Obviously the means for outputting O and the means for inputting I may not necessarily form part of the apparatus but may also be embodied by an external device able to communicate with the dialysis machine A. E.g. the means may be embodied by a smart phone or smart tablet or notebook being enabled with a respective interface such as NFC, Bluetooth, ZigBee, W-Lan and being provisioned with a respective user interface for communicating with the dialysis machine A such as an App.

Provisioning of input means allow for entering security codes, patient identity data, and treatment data and may therefore enhance security of the devices.

In particular the means for inputting I towards the reusable disposable 1 may also comprise a card reader CR and/or a NFC reader NFC and/or an RFID reader RFID.

By usage of these inputting means, also data from the disposable may be read as well as data related to a patient may be read allowing for an I.e. according to aspects of the invention it is provided for storing information about a product, about a possible reuse as well as a real usage.

Information can be read by the dialysis machine A used for treatment and based on the information available in the reusable disposable 1 the dialysis machine A may permit or block a treatment.

In a first memory $MEM_1$ one may store product information that cannot be changed later on and shall be written before the shipment or in the production process. This information may comprise a brand name, an article number, a lot number and other relevant product information.

As a security measure allowing for a hardware and/or software lock a Checksum may be stored to guaranty that the content of the memory is safe.

In a second memory $MEM_2$ information relating to a maximum usage of the reusable disposable 1 may be stored before the shipment or in production process. This information may comprise a maximum number of usages, a maximum operation time, an expiration date/best-before date, and. any other type of value that can be used to determine a limit for the usage of the reusable disposable 1.

As a security measure allowing for a hardware and/or software lock a Checksum may be stored to guaranty that the content of the memory is safe.

In a third memory $MEM_3$ one may store information about the (past) usage of the reusable disposable 1. This usage may be secured against re-writing. I.e. information stored may not be erased. Such information may also be stored in fuse like arrays, where a fuse is burned each time a certain period/amount has lapsed.

To guaranty safety an ID of a Patient may be stored. This is representing the Patient ID and will be used to guaranty that this consumable can be used in future only for the same patient. Such information may be provided by means for inputting I as detailed above. E.g. a card reader CR may be provided reading an insurance card of a patient identifying thereby the patient.

To trace usage each time the treatment start the dialysis machine A may write a log into a third memory $MEM_3$ of the reusable disposable 1, e.g. a start date and time, duration of a usage, end date and time, machine serial number or other treatment relevant information.

As a security measure allowing for a hardware and/or software lock a Checksum may be stored to guaranty that the content of the memory is safe.

The dialysis machine A interacting with the reusable disposable 1 may be enabled to read information stored in the reusable disposable 1 and check if is the first usage or if the disposable was already used in the past. The interfacing may be provided by any kind of connection (direct, optical or wireless etc.)

If the reusable disposable 1 is used for the first time, a Patient ID is stored in the reusable disposable 1. Additional information relating to the usage may be stored during and/or after treatment in a respective memory.

In case the reusable disposable 1 was already used the past, a dialysis machine A and/or the reusable disposable 1 may check if the patient ID stored in reusable disposable 1 correspond to a patient ID actually provided. In case the patient ID does not correspond treatment is inhibited and additionally a warning may be provided either via a means for display and/or be emitting a warning sound.

Furthermore, it may also be checked whether the reusable disposable 1 may still safely be used. I.e. the dialysis machine and/or the reusable disposable 1 may check if the reusable disposable 1 has not reach the end of usage. End of usage may be a hard condition such as a best-before date or a soft-condition such as a maximum number of treatments.

Furthermore, if a treatment would consume more than the maximum usage, such a usage may be inhibited in order not to risk an incomplete treatment.

By means of the invention it is provided for a reuse of disposables in a safe way, such that there is no risk that a disposable may be used by another patient.

Furthermore, by means of the invention it is provided for a maximum usage of the disposable thereby allowing for guaranteeing quality of the reusable disposable 1.

By means of the invention it may also be provided for tracing relevant disposable information (Lot Number etc.), e.g. by reporting usage data towards a back-end system.

As the system of reusable disposable 1 and dialysis machine are co-operating there is no need for further external IT systems as all checks may be performed by the reusable disposable 1 and/or the dialysis machine A.

As a further benefit, storage of product data may also allow for a simplified tracking of products within pharmacies, dealers, health care providers, etc.

Although the invention has been described with respect to renal dialysis and/or liver dialysis the invention is not limited thereto. Likewise, the invention may also be employed with respect to other forms of therapy employing disposables such as Citrate-Calcium therapy.

The invention claimed is:

1. A reusable disposable apparatus for usage, within a medical treatment process, by a corresponding medical apparatus (A), the reusable disposable apparatus comprising:
   first memory for storing predetermined data, whereby the first memory is a write-once memory and is programmed during production of the reusable disposable apparatus, whereby the first memory is secured against unauthorized alteration after the production, the first memory being fixedly attached to the reusable disposable apparatus; and
   second memory for storing patient identity data, whereby the second memory is a write-once memory, the second memory being fixedly attached to a disposable part of the reusable disposable apparatus;
   wherein re-usage of the reusable disposable apparatus is only allowed with respect to the same patient identity data, and the first memory comprises a software lock and a hardware lock thereby preventing unauthorized alteration of data contained in the first memory after storage,
   and wherein patient identity data is stored in the second memory before, during, or after dialysis, and re-usage of the reusable disposable apparatus is controlled by the reusable disposable apparatus according to predetermined data in the first memory and the second memory.

2. The reusable disposable apparatus according to claim 1, wherein the first memory comprises data that is at least one member selected from the group consisting of brand, article number, lot, and security code.

3. The reusable disposable apparatus according to claim 1, wherein the first memory comprises predetermined data that is at least one member selected from the group consisting of maximum number of usages, maximum run time, best before date, and security code.

4. The reusable disposable apparatus according to claim 1, further comprising a third memory wherein the third memory comprises a log of treatment related data.

5. The reusable disposable apparatus according to claim 4, wherein the third memory comprises a software lock for preventing unauthorized alteration of data contained in the third memory after storage.

6. The reusable disposable apparatus according to claim 1, wherein the second memory comprises a software lock for preventing unauthorized alteration of data contained in the second memory after storage.

7. The reusable disposable apparatus according to claim 1, wherein the medical treatment process is a dialysis process and the corresponding medical apparatus (A) is a dialysis apparatus.

8. A medical apparatus (A) for usage of the reusable disposable apparatus according to claim 1 within a medical treatment process, the medical apparatus (A) comprising:
   means for reading data from the first memory of said reusable disposable apparatus; and
   means for reading data from the second memory of said reusable disposable apparatus;
   wherein re-usage of the reusable disposable apparatus is only allowed with respect to the same patient identity data, the means for reading data from the first memory is an RFID reader, and the means for reading data from the second memory is an RFID reader.

9. The medical apparatus (A) according to claim 8, wherein the reusable disposable apparatus further comprises a third memory, and the medical apparatus (A) comprises means for storing data in the third memory.

10. The medical apparatus (A) according to claim 9, wherein the third memory comprises a software lock for preventing unauthorized alteration of data contained in the third memory after storage.

11. The medical apparatus (A) according to claim 8, wherein re-usage of the reusable disposable apparatus is also controlled by the medical apparatus (A).

12. The medical apparatus (A) according to claim 9, wherein the medical apparatus (A) further comprises a display (0) for displaying data stored in the first memory, the second memory, the third memory, or a combination thereof.

13. The medical apparatus (A) according to claim 9, wherein the medical apparatus (A) further comprises means for inputting (I) data for storing in said second memory and/or third memory, and the third memory means comprises a log of treatment related data.

14. The medical apparatus (A) according to claim 8, wherein the means for inputting (I) comprises a card reader (CR), an NFC reader (NFC), an RFID reader (RFID), or a combination thereof.

15. The reusable disposable apparatus according to claim 1, further comprising a valve, a pump, a membrane, or a combination thereof.

* * * * *